(12) United States Patent
Chong

(10) Patent No.: US 6,426,081 B1
(45) Date of Patent: Jul. 30, 2002

(54) COSMETIC FIRMING FORMULATION

(76) Inventor: Myong Hun Chong, 6114 Pennsylvania Ave., Arlington, TX (US) 76017

( * ) Notice: Subject to any disclaimer, the term of this patent is extended or adjusted under 35 U.S.C. 154(b) by 0 days.

(21) Appl. No.: 09/723,586

(22) Filed: Nov. 28, 2000

Related U.S. Application Data

(60) Provisional application No. 60/168,257, filed on Nov. 30, 1999.

(51) Int. Cl.$^7$ .................................................. A61K 7/00
(52) U.S. Cl. ........................ 424/401; 424/725; 424/728; 424/732; 424/738; 424/736; 424/744; 424/771
(58) Field of Search .................................. 424/725, 401

(56) References Cited

U.S. PATENT DOCUMENTS

| | | | | |
|---|---|---|---|---|
| 5,540,853 A | * | 7/1996 | Trinh et al. | |
| 5,578,312 A | * | 11/1996 | Parrinello | |
| 5,723,138 A | * | 3/1998 | Bae et al. | |
| 5,747,006 A | * | 5/1998 | Dornoff et al. | |
| 5,925,348 A | * | 7/1999 | Riley et al. | |
| 5,932,230 A | * | 8/1999 | DeGrate | |
| 6,147,054 A | * | 11/2000 | De Paoli | |
| 6,197,343 B1 | * | 3/2001 | Minami et al. | |

* cited by examiner

*Primary Examiner*—Leon B. Lankford, Jr.
*Assistant Examiner*—Ruth A. Davis
(74) *Attorney, Agent, or Firm*—Bracewell & Patterson, LLP

(57) ABSTRACT

A cosmetic formulation is shown which includes aloe vera and as well as Vitamins A,C and E as essential ingredients. The formulations penetrate the epidermis to aid in reducing pores, renewing the skin and create a smoother texture.

2 Claims, No Drawings

COSMETIC FIRMING FORMULATION

CROSS REFERENCE TO RELATED APPLICATION

This application claims priority based upon provisional application no. 60/168,257,filed Nov. 30, 1999,by the same inventor and entitled "Cosmetic Rejuvenating and Healing Product, Method For Its Manufacture And Uses Thereof."

BACKGROUND OF THE INVENTION

1. Field of the Invention

The present invention relates to a cosmetic composition for rejuvenating the appearance of skin with reduced or minimal potential for skin irritation, preferably in the form of a lotion or serum which includes aloe vera as well as Vitamins A,C and E.

2. Description of the Prior Art

Conventional treatment of, or attempted prevention of, normal tissue damage caused by, for example, UV radiation of the sun, over-exfoliated, peeled and lasered skin tissue, and the like, is currently confined to the application of bland moisturizing creams designed only to minimize infection to the damaged site or to prevent itching and subsequent scratching by the affected individual. Such treatment can at best only offer symptomatic relief and a barrier to assist prevention of secondary infection at the affected site.

Additionally, conventional creams or ointments are designed to deliver an active component only to the epidermal surface of the skin or, at best, to provide limited delivery through the surface skin layers. Because these existing formulations are presented to the epidermal surface in a form likely to penetrate only into the outer layer of the epidermis, they fail to provide a deep healing effect.

A need exits, therefore, for a cosmetic formulation which will treat all skin types deep beneath the surface layer of the epidermis to reduce pores, renew the skin and create a smoother texture.

A need also exists for such a cosmetic formulation which will stimulate melatonin production and counteract sun damage to the skin, thereby promoting healing and returning the skin to a normal, healthy level.

A need also exists for such a cosmetic formulation which relieves itching and other discomforts suffered after laser or face lift surgery and glycolic or chemical peels which acts swiftly to aid the healing process immediately upon contact.

SUMMARY OF THE INVENTION

The present invention is a cosmetic composition for rejuvenating the appearance of skin with reduced or minimal potential for skin irritation, preferably in the form of a lotion or serum, which includes as essential components aloe vera as well as vitamins A, C and E. The composition is especially recommended for thick, aging skin, enlarged pores and dehydrated or sun damaged skin.

Additional objects, features and advantages will be apparent in the written description which follows.

DETAILED DESCRIPTION OF THE INVENTION

The cosmetic formulation of the invention is formulated to reduce pores, renew the skin and create a smoother texture. It is an excellent pre-op treatment for laser surgery, face lifts, glycolic and chemical peels. It is particularly recommended for thick, aging skin, enlarged pores and dehydrated or sundamaged skin. In the preferred form of a liquid or semi-liquid serum, it can be applied by saturating a cotton ball and using the ball to apply the formulation to the neck and face area. The cosmetic formulations are also beneficial in treating the deleterious effects of glycolic or chemical peels, and relieve itching after laser surgery or face lift surgery immediately upon contact. While other products cleanse and moisturize at the surface level, the formulations of the present invention restores, balances and hydrates the human epidermis at a deeper level, returning it to its normal healthy state.

The cosmetic formulation of the invention utilizes pure botanical essences and vitamins to provide a gentle, fragrant and soothing composition which aids the skins ability to heal itself. The formulations of the invention nurture and nourish the skin so that within a short period of time the skin appears younger, healthier, more firm and glowing.

The cosmetic formulations of the invention include aloe vera as an essential component. Aloe vera is a well known extract from the aloe plant and occurs naturally in nature. The aloe leaf consists of three primary sections: the rind (photosynthesis) with sap contained in the pericyclic transport tubules (xylem and phloem), the mucilage (container) layer and the parenchyma or gel fillet (storage) layer. It is believed that the beneficial properties of the plant extract are the result of the synergistic actions of at least 75 known ingredients, including polysaccharides, steroids, organic acids, enzymes, antibiotic agents, amino acids and minerals. Glucomannan, one special complex polysaccharide composed largely of the sugar mannose, interacts with special cell-surface receptors on those cells which repair damaged tissues, called fibroblasts, stimulating them, activating their faster growth and replication. Plant hormones in aloe, called gibberellins, also accelerate healing by cell replication. Various other beneficial effects of the aloe vera plant extract are reported in the literature. The aloe vera component of Applicant's formulation is present in the range from about 10 to 20% by volume, most preferably about 16% by volume, based upon the total volume of the cosmetic formulation.

Applicant's cosmetic formulations present the positive healing properties of the aloe extract in combination with a synergistic active ingredient formulation which allows the active ingredients to penetrate more deeply into the epidermis to provide a deeper, longer lasting healing effect. The additional components of the formulation will be discussed in turn below.

The formulations of the invention include as one component, a commercially available multi-fruit blend comprising bilberry extract, sugar cane, sugar maple, orange and lemon extract. Bilberry concentrate is prepared to specifically contain at least 25% anthocyanosides. Anthocyanoside is one of the more effective antioxidants. In fact, it is generally ranked higher in anti-oxidant power than Vitamins E and C by some experts. The bilberry/fruit extract component of the formulations serves as a moisturizer and exfoliant as well as offering fruit anti-oxidant properties and is present in the range from about 5 to 15% by volume, most preferably about 10% by volume, based upon the total volume of the formulation.

Propylene glycol is a commonly used moisture carrying vehicle and is used as a humectant in the formulations of the invention. It is present in the range from about 1 to 5% by volume, most preferably about 3% by volume, based upon the total volume of formulation.

Sodium hyaluronate is a sterile mixture made up mostly of natural, highly purified sodium hyaluronate that comes from rooster combs. It is available from a number of commercial sources and is present in the formulations of the present invention in the range from about 1 to 5% by volume, most preferably about 2% by volume, based upon the total volume of the formulation.

Ascorbic acid is a commercially available form of the anti-oxidant Vitamin C and is present in the range from about 1 to 5% by volume, most preferably about 2% by volume.

Hydroxyethycellulose is one of several fibrous substances consisting of the chief part of the cell walls of plants. This family of materials is used as emulsifiers in creams and lotions and is resistant to bacterial decomposition and gives uniformity to the product. This component is present in the range from about 0.5 to 5% by volume, most preferably about 1.2% by volume, based upon the total volume of formulation.

Imidazolidinyl urea is a commercially available preservative present in the formulations of the invention in the range from about 0.01 to 0.5% by volume, most preferably about 0.2% by volume.

Camomile is a well known herb which supplies an apple aroma as a fragrance to cosmetic formulations. It's extract also supplies anti-inflammatory properties to the formulations of the invention and is present in the range from about 0.1 to 1.0% by volume, most preferably about 0.5% by volume.

Polysorbate-20 is a commercially available emulsifier associated with stearic acid. It is present in the formulations of the invention in the range from about 0.1 to 1.0% by volume, most preferably about 0.5% by volume, based upon the total volume of the formulation.

Methylparaben is a widely used preservative in cosmetics. It has broad spectrum antimicrobial activity and is non-irritating and non-toxic. It is present in the range from about 0.05 to 1.0% by volume, most preferably about 0.15% by volume.

Ginseng is an herb which possesses nutritional compounds which rejuvenate the body. Cultivation in North America began in the $19^{th}$ Century. Ginseng contains ginsenocides, protein, carbohydrates, sugars, vitamins and minerals in varying amounts. Ginseng extract, from a commercial source, is present in the formulations of the invention in the range from about 0.5 to 5% by volume, most preferably about 1.0% by volume.

Tocopheryl acetate is a source of Vitamin E. It has known antioxidant properties and is present in the range from about 0.01 to 0.5% by volume, most preferably about 0.1% by volume.

Retinyl palmitate is the ester of Vitamin A and palmitic acid. It is present in the range from about 0.05 to 0.5% by volume, most preferably about 0.1% by volume.

In a particularly preferred form, the cosmetic rejuvenating formulation of the invention comprises:

| INGREDIENT | FUNCTION | PERCENTAGES |
|---|---|---|
| 1. ALOE VERA GEL | MOISTURIZER HEALING | 16.0 |
| 2. D.I. WATER | SOLVENT | 63.25 |
| 3. BILBERRY EXT & SUGAR CANE SUGAR MAPLE EXT & ORANGE EXT LEMMON EXT (MULTI-FRUIT BSC) | MOISTURIZER EXFOLIANT & FRUIT ACIDS | 10.0 |
| 4. PROPYLENE GLYCOL | HUMECTANT | 3.0 |
| 5. SODIUM HYALURONATE | SKIN CONDITIONER | 2.0 |
| 6. ASCORBIC ACID | ANTIOXIDANT, VITAMIN C | 2.0 |
| 7. HYDROXYETHYL CELLULOSE | THICKENER | 1.2 |
| 8. IMIDAZOLIDINYL UREA | PRESERVATIVE | 0.2 |
| 9. CHAMOMILE EXT | ANTI-INFLAMMATORY, REFRESHING | 0.5 |
| 10. POLYSORBATE -20 | EMULSIFIER | 0.5 |
| 11. METHYLPARABEN | PRESERVATIVE | 0.15 |
| 12. GINSENG EXT | HEALING, NOURISHING, TONIC | 1.0 |
| 13. TOCOPHERYL ACETATE | ANTIOXIDANT, VITAMIN E | 0.1 |
| 14. RETINYL PALMITATE | SKIN CONDITIONER, VITAMIN A | 0.1 |

A pilot study was undertaken to evaluate the formulations of the invention on human skin keratinocytes.

Objective: The purpose of the pilot study was to determine if it is possible to evaluate biological effects of the cosmetic formulations of the invention on human skin by in vitro methods using cells and tissue equivalents.

Methods: Samples were formulated according to the above Table. The samples were added to 0.4 micron Millipore filters and placed in liquid cultures (24 or 6 well-culture plates) with the sample side up. The active components were thus not in direct contact with the human skin cells (keratinocytes) which were grown on the bottom of the culture dishes. Controls received filter discs but with no added vehicle or any control cream/liquid. Samples were incubated at 37° C. in the usual fashion and samples were assayed for cell viability using the neutral red dye uptake assay.

Results: In the first set of studies, approximately 20 μl of the cosmetic formulation of the invention were added to the filters and placed in culture with the cells. After 24 hours, most of the cells (>90%) remained alive. The melanocytes were noted to be stimulated in production of melanin.[1]

[1] In the case of the AHA Firming Lotion, it was noted that the solution dropped the pH of the media below 7 and this had to be readjusted.

In a second set of studies, six well plates were used with larger numbers of cells (approximately 300,000). The formulations of the invention were used at 20 and 40 μl per well. Samples were incubated for 5 days as above. In these cases, cells were harvested and viable cells counted for quantitation. It was noted that the formulations of the invention caused only a small decrease in viability (e.g., controls =180,000 vs. samples =150,000). This was more pronounced at 40 µl (87,000 viable cells). There is at least some evidence in the testing which has been completed that the formulations of the invention promote some cell activation (melanocytes).

An invention has been provided with several advantages. The formulations of the invention contain primarily natural ingredients yet penetrate the epidermis to provide improved healing properties to reduce pores, renew the skin and create a smoother textured skin. The formulations provide improved healing properties and serve as excellent pre-op treatments for persons undergoing surgical skin procedures, face lifts, glycolic and chemical peels and similar procedures. The unique combination of Vitamins A,C and E with the other natural ingredients produces a synergistic effect in achieving the desired results mentioned above.

While the invention has been shown in only one of its forms, it is not thus limited but is susceptible to various changes and modifications without departing from the spirit thereof.

I claim:

1. A cosmetic formulation, comprising a liquid serum containing:

from about 10 to 20% by volume, based upon the total volume of formulation of aloe vera gel;

from about 5 to 10% by volume of the cosmetic formulation of a commercially prepared extract, the extract containing bilberry, sugar cane, sugar maple, orange and lemon extracts;

from about 1 to 5% by volume of propylene glycol;

from about 1 to 5% by volume of ascorbic acid;

from about 1 to 5% by volume of sodium hyaluronate;

from about 0.5 to 5% by volume of hydroxyethylcellulose;

from about 0.5 to 5% by volume of Ginseng extract;

from about 0.05 to 1.0% by volume of tocopheryl acetate; and from about 0.05 to 1.0% by weight of retinyl palmitate; and the balance being selected preservatives and deionized water.

2. The formulation of claim 1, further comprising as emulsifiers and preservatives:

from about 0.1 to 1.0% by volume of polysorbate-20;

from about 0.05 to 0.5% by volume of imidazolidinyl urea;

from about 0.05 to 0.5% by volume of methylparaben.

* * * * *